United States Patent [19]

Ayad

[11] 4,438,110

[45] Mar. 20, 1984

[54] CHEWING INSECT TOXICANT COMPOSITIONS

[75] Inventor: Hafez M. Ayad, Cary, N.C.

[73] Assignee: Union Carbide Corporation, Danbury, Conn.

[21] Appl. No.: 372,668

[22] Filed: Apr. 28, 1982

Related U.S. Application Data

[72] Continuation-in-part of Ser. No. 278,722, Jun. 29, 1981, now abandoned.

[51] Int. Cl.³ .................. A01N 57/02; A01N 47/28
[52] U.S. Cl. ............................ 424/217; 424/225; 424/322
[58] Field of Search .................. 424/322, 225, 217

[56] References Cited

U.S. PATENT DOCUMENTS

| | | | |
|---|---|---|---|
| 3,138,522 | 6/1981 | Plapp et al. | 424/225 |
| 3,748,356 | 7/1973 | Wellinga et al. | 424/322 |
| 4,139,636 | 2/1979 | Sirrenberg et al. | 424/322 |
| 4,162,330 | 7/1979 | Ehrenfreund | 424/322 |
| 4,173,637 | 11/1979 | Nishiyama et al. | 424/322 |
| 4,277,499 | 7/1981 | Sirrenberg et al. | 424/322 |

OTHER PUBLICATIONS

Pimprikar and Georghiou, Pesticide Biochemistry and Physiology, vol. 12, No. 1, 1979, pp. 10-22.

*Primary Examiner*—Delbert R. Phillips
*Assistant Examiner*—F. T. Moezie
*Attorney, Agent, or Firm*—R. C. Brown; J. A. Shedden

[57] ABSTRACT

This invention relates to chewing insect toxicant compositions comprising (1) a 1-(mono-substituted phenyl)-3-benzoyl urea compound in admixture with (2) an amount sufficient to enhance the chewing insect toxicity of said urea compound of a phosphorous-containing compound. This invention is also directed to chewing insect toxicant compositions comprising an acceptable carrier and as the active toxicant an effective amount of the composition of this invention as well as to a method of controlling insects by subjecting them to an effective amount of the composition of this invention.

37 Claims, No Drawings

CHEWING INSECT TOXICANT COMPOSITIONS

FIELD OF THE INVENTION

This invention relates to chewing insect toxicant compositions comprising 1-(mono-substituted phenyl)-3-benzoyl urea compounds in admixture with a phosphorous-containing compounds. The compositions have greatly enhanced biological activity on chewing insects in comparison with the combined biological activity exhibited by the 1-(mono-substituted phenyl)-3-benzoyl urea compound alone and the phosphorous-containing compound alone at specified concentration amounts.

BACKGROUND OF THE INVENTION

The development of new methods for increasing the biological activity of agricultural insecticides is an active field of research. Researchers in this field endeavor to develop new combinations of insecticidal compositions, e.g., mixtures of insecticidal compounds with other known agricultural ingredients, mixtures of insecticidal compounds with synergistic compounds and the like, having enhanced biological activity in comparison with the combined additive biological activity of the individual components thereof. U.S. Pat. No. 4,173,637 and U.S. Pat. No. 3,748,356 teach that mixtures of the insecticidal compounds described therein, e.g., substituted benzoyl urea compounds, with other known agricultural ingredients may produce synergistic effects. Several articles report the use of synergistic compounds, e.g., phosphorous-containing compounds, which may enhance the toxicity of insecticidal compounds in combination therewith. See Plapp Jr., Bigley, Chapman and Eddy, Journal of Economic Entomology, Vol. 56, No. 5, 1963, pages 643–649; Attia, Shenahan and Shipp, Journal of Economic Entomology, Vol. 73, No. 2, 1980, pages 184–185; and Pimprikar and Georghiou, Pesticide Biochemistry and Physiology, Vol. 12, No. 1, 1979, pages 10–22. This field of research is important not only for fulfilling such important objectives and eliminating undesirable insects, combatting a wide variety of insecticide-resistant insects, enhancing the harvested quantity of crops and the like, but also from an economic and environmental point of view in reducing the amount of active ingredient normally required for the particular application.

However, researchers have found that synergistic insectidal activity can only be positively determined by experimentation. Certain combinations of insecticidal compositions, e.g., mixtures of insectidical compounds with other known agricultural ingredients or mixtures of insecticidal compounds with known synergistic compounds at specified concentration amount, may unexpectedly exhibit no synergistic activity whereas other combinations of insecticidal compositions at the same concentration amounts may unexpectedly exhibit synergistic activity. Surprisingly, as a result of extensive research in the development of new methods for increasing the biological activity of agricultural insecticides, the present invention provides chewing insect toxicant compositions comprising a 1-(mono-substituted phenyl)-3-benzoyl urea compound in admixture with a phosphorous-containing compound as structurally depicted below. These compositions have greatly enhanced biological activity on chewing insects in comparison with the combined additive biological activity of the 1-(mono-substituted phenyl)-3-benzoyl urea compound alone and the phosphorous-containing compound alone at specified concentration amounts.

SUMMARY OF THE INVENTION

In accordance with the teachings of the present invention, chewing insect toxicant compositions are provided comprising (1) a mono-substituted phenyl benzoyl urea compound having the formula:

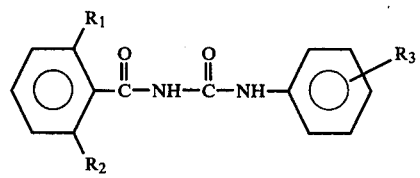

in admixture with (2) an amount sufficient to enhance the chewing insect toxicity of said urea compound of a phosphorous-containing compound having the formula:

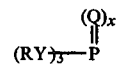

wherein:
R is:
an alkyl group having no more than ten carbon atoms, or aryl or aryl substituted with alkyl or alkoxy;
$R_1$ and $R_2$ are independently:
hydrogen, or
halogen;
$R_3$ is:
halogen,
an alkyl, haloalky, alkoxy, or
haloalkoxy group having no more than eight carbon atoms,
a pyridyloxy group, or
a halopyridyloxy group;
Y and Q are independently:
oxygen, or
sulfur; and
x is:
zero, or
one.

The chewing insect toxicant compositions of this invention provide more effective kill of chewing insects than would be expected from the combined additive kill of the urea compound alone and the phosphorous-containing compound alone at specified concentration amounts. The phosphorous-containing compounds act as synergists which, although having little or no direct toxic effect per se at specified concentration amounts employed, are able to substantially enhance the chewing insect toxicity of the 1-(mono-substituted phenyl)-3-benzoyl urea compound with which they are combined.

This invention further provides a chewing insect toxicant composition comprising an acceptable carrier and as the active toxicant an effective amount of the composition as described above.

This invention still further relates to a method of controlling chewing insects which comprises subjecting them to an effective amount of the composition as described above.

DESCRIPTION OF THE PREFERRED EMBODIMENTS

The chewing insect toxicant compositions of this invention contain, as an essential component, a 1-(mono-substituted phenyl)-3-benzoyl urea compound having the formula,

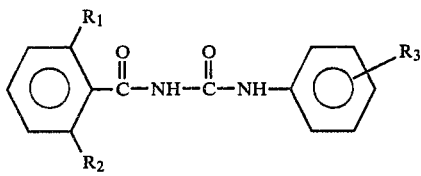

$R_1$ and $R_2$ are independently:
hydrogen, or
halogen;
$R_3$ is:
halogen,
an alkyl, haloalky, alkoxy, or
haloalkoxy group having no more than eight carbon atoms,
a pyridyloxy group, or
a halopyridyloxy group;

The generally preferred 1-(mono-substituted phenyl)-3-benzoyl urea compounds are those wherein $R_1$ and $R_2$ are independently hydrogen, chloro or fluoro and $R_3$ is chloro, fluoro, bromo, an alkyl, haloalkyl, alkoxy, or haloalkoxy group having no more than three carbon atoms, a pyridyloxy group, or a halopyridyloxy group. Most preferred are the substituted benzoyl urea compounds encompassed by the formula when $R_1$ and $R_2$ are independently hydrogen, chloro ro fluoro and $R_3$ is chloro, trifluoromethyl, trifluoromethoxy or 3,5-dibromopyridyl-2-oxy.

Illustrative of the preferred 1-(mono-substituted phenyl)-3-benzoyl urea compounds are as follows:
N-(2,6-difluorobenzyl)-N'-(4-chlorophenyl)urea
N-(2,6-difluorobenzyl)-N'-(4-bromophenyl)urea
N-(2,6-difluorobenzyl)-N'-(4-fluorophenyl)urea
N-(2,6-difluorobenzyl)-N'-(4-trifluoromethylphenyl)urea
N-(2,6-difluorobenzyl)-N'-(4-isopropylphenyl)urea
N-(2,6-difluorobenzyl)-N'-(4-t.butylphenyl)urea
N-(2,6-difluorobenzyl)-N'-(4-n-butylphenyl)urea
N-(2,6-difluorobenzyl)-N'-(4-iodophenyl)urea
N-(2,6-difluorobenzyl)-N'-(3-trifluoromethylphenyl)urea
N-(2,6-dichlorobenzyl)-N'-(4-chlorophenyl)urea
N-(2,6-dichlorobenzyl)-N'-(4-bromophenyl)urea
N-(2,6-dichlorobenzyl)-N'-(4-fluorophenyl)urea
N-(2,6-dichlorobenzyl)-N'-(4-trifluorophenyl)urea
N-(2,6-dichlorobenzyl)-N'-(4-isopropylphenyl)urea
N-(2,6-dichlorobenzyl)-N'-(4-t.butylphenyl)urea
N-(2,6-dichlorobenzyl)-N'-(4-n-butylphenyl)urea
N-(2,6-dichlorobenzyl)-N'-(4-iodophenyl)urea
N-(2,6-dichlorobenzyl)-N'-(3-trifluoromethylphenyl)urea
N-(2,6-dichlorobenzyl)-N'-(4-ethylphenyl)urea
N-(2-chlorobenzoyl)-N'-[4-(3,5-dibromopyridyl-2-oxy)-phenyl]urea
N-(2-chlorobenzoyl)-N'-[4-(3,5-dichloropyridyl-2-oxy)-phenyl]urea
N-(2-chlorobenzoyl)-N'-[4-(5-bromopyridyl-2-oxy)phenyl]
N-(2,6-dichlorobenzoyl)-N'-[4-(3,5-dichloropyridyl-2-oxy)phenyl]urea
N-(2,6-difluorobenzoyl)-N'-[4-(3,5-dichloropyridyl-2-oxy)phenyl]urea
1-(4-trifluoromethoxyphenyl)-3-(2-chlorobenzoyl)urea
1-4-trifluoromethoxyphenyl)-3-(2,6-dichlorobenzoyl)urea
1-(4-trifluoromethoxyphenyl)-3-(2,6-difluorobenzoyl)urea
N-[4-(2-chloro-1,1,2-trifluoroethoxy)phenyl]-N'-(2,6-difluorobenzoyl)urea Illustrative of the most preferred 1-(mono-substituted phenyl)-3-benzoyl urea compounds suitable as components in the chewing insect toxicant compositions of this invention include the following:
N-(2,6-difluorobenzoyl)-N'-(4-chlorophenyl)urea
N-(2-chlorobenzoyl)-N'-[4-(3,5-dibromopyridyl-2-oxy)-phenyl]urea
1-(4-trifluoromethoxyphenyl)-3-(2-chlorobenzoyl)urea The chewing insect toxicant compositions of this invention also contain, as an essential component, a phosphorous-containing compound having the average formula,

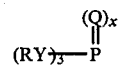

wherein:
R is:
an alkyl group having no more than ten carbon atoms, or
aryl or aryl substituted with alkyl or alkoxy;
Y and Q are independently:
oxygen, or
sulfur; and
x is:
zero, or
one.

The phosphorous-containing compounds act as synergists and effectively enhance the biological activity of the 1-(mono-substituted phenyl)-3-benzoyl urea compounds with which they are combined. The generally preferred phosphorous-containing compounds are those wherein R is methyl, ethyl, isopropyl, butyl, phenyl or tolyl, Q and Y are independently oxygen or sulfur and x is one. Most preferred are the phosphorous-containing compounds encompassed by the formula when R is butyl or phenyl, Q is oxygen, Y is oxygen or sulfur and x is one.

Illustrative of the preferred phosphorous-containing compounds are as follows:
Triethyl phosphate
Triethyl phosphite
Tributyl phosphate
Tributyl phosphite
Triphenyl phosphate
Triphenyl phosphite
Tri-p-tolyl phosphate
Tri-p-totyl phosphite
Tri-m-totyl phosphate
Tri-o-totyl phosphate
Tri-o-totyl phosphorothioate
S,S,S-tributyl phosphorotrithioate
S,S,S-tributyl phosphorotrithioite
Trimethyl phosphorotetrathioate
Triethyl phosphorotetrathioate
Triisopropyl phosphorotetrathioate Tributyl phosphorotetrathioate
Tris (1-methylbutyl)phosphorotetrathioate Illustrative of the most preferred phosphorous-containing compounds suitable as compounds in the compositions of this invention include the following:
Triphenyl phosphate
S,S,S-tributyl phosphorotrithioate The most preferred compositions of this invention include an effective amount of a specified 1-(mono-substituted phenyl)-3-benzoyl urea compound in admixture with an effective amount of a specified phosphorous-containing compound as follows: (1) N-(2,6-difluorobenzoyl)-N'-(4-chlorophenyl)urea in admixture with triphenyl phosphate; (2) N-(2-chlorobenzoyl)-N'-[4-(3,5-dibromopyridyl-2-oxy)phenyl]urea in admixture with triphenyl phosphate; (3) 1-(4-trifluoromethoxyphenyl)-3-(2-chlorobenzoyl)urea in admixture with triphenyl phosphate; (4) N-(2,6-difluoro-benzoyl)-N'-(4-chlorophenyl)urea in admixture with S,S,S-tributyl-phosphorotrithioate; (5) N-(2-chlorobenzoyl)-N'-[4-(3,5-dibromopyridyl-2-oxy)phenyl]urea in admixture with S,S,S-tributylphosphorotrithioate; and (6) 1-(4-(trifluoromethoxyphenyl)-3-(2-chlorobenzoyl)urea in admixture with S,S,S-tributylphosphorotrithioate.

The compositions of the present invention can be prepared by several methods which are known in the art (e.g., by mixing a substituted benzoyl urea compound with a phosphorous-containing compound in specified concentration amounts). The 1-(mono-substituted phenyl)-3-benzoyl urea compounds utilized as an essential component in the compositions of this invention are known materials made by known methods as described in U.S. Pat. No. 4,173,637, U.S. Pat. No. 3,748,356 and U.S. Pat. No. 4,139,636. The phosphorous-containing compounds utilized as an essential component in the compositions of this invention are also known material made by known methods.

The 1-(mono-substituted phenyl)-3-benzoyl urea compound and the phosphorous-containing compound are mixed in specifically defined weight proportion ratios to produce the chewing insect toxicant compositions of this invention. The weight proportion of the urea compound to the phosphorous-containing compound can vary over a wide range depending on such factors as the particular locus to be treated, the particular pest to be combatted and the particular effect desired. The weight proportion ratio of the urea compound to the phosphorous-containing compound is from about 1:5 to about 1:50000 parts by weight respectively. The weight proportion ratio may be, for example, from 1:100 to 1:40000. Preferably, the weight proportion ratio of 1-(mono-substituted phenyl)-3-benzoyl urea compound to the phosphorous-containing compound is from about 1:40 to about 1:30000 parts by weight respectively.

The composition of this invention are effective against a wide variety of chewing insects. It is understood that the Southern armyworm evaluated in the working Examples herein is representative of a wider variety of chewing insect which can be controlled by the compositions of this invention. These compositions are particularly useful in controlling insects of agricultural crops, e.g., potatoes, maize, sugar beets, cotton, rice, wheat, tobacco, soybeans, deciduous and citrus fruits.

The compositions contemplated in this invention may be applied as chewing insect insecticides according to methods known to those skilled in the art. Insecticides containing these compositions as the active toxicant will usually comprise a carrier and/or diluent, either liquid or solid. One suitable method of preparing the compositions for application is to mix the phosphorous-containing compound with or without solvent or diluent, with a suitable carrier and then mix the resulting mixture with the 1-(mono-substituted phenyl)-3-benzoyl urea compound with or without solvent.

Suitable liquid diluents or carriers include water, petroleum distillates, or other liquid carriers with or without surface active agents. Liquid concentrates may be prepared by dissolving one of these compositions with a non-phytotoxic solvent such as acetone, xylene, or nitro-benzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as natural clay, talc, pyrophyllite, bentonite, diatomaceous earth, fullers earth, corn cobs, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentration will usually vary from about 10 to 95 percent by weight and in the solid formulations from about 0.5 to about 90 percent by weight. Satisfactory sprays, dusts, or granules for general use contain from about $\frac{1}{4}$ to 15 pounds of active toxicant per acre.

The compositions contemplated herein prevent attachment by insects upon plants or other material to which the compositions are applied. With respect to plants, they have a high margin of safety in that when used in sufficient amount to kill or repel the chewing insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable characteristics of the toxicants or impart undesirable characteristics, for instance, phytotoxicity, to the toxicants. The toxicants are compatible with other constituents of the spray schedule, and they may be used in the soil, upon the seeds, or the roots of plants without injuring either the seeds or roots of plants. Mixtures of the compositions of this invention may be employed if desired as well as combinations of the compositions with one or more fungicides, bactericides, acaricides, nematocides, insecticides or other biologically active compounds.

The following examples are illustrative of the present invention and are not intended as a limitation upon the scope thereof.

In accordance with Examples 1 to 39 inclusive, the following 1-(mono-substituted phenyl)-3- benzoyl urea compounds and phosphorous-containing compounds are employed as essential components in the preparation of the chewing insect toxicant compositions of this invention.

Substituted Benzoyl Urea Compound I (SBUC I):
 N-(2,6-difluorobenzoyl)-N'-(4-chlorophenyl)urea
Substituted Benzoyl Urea Compound II (SBUC II):
 N-(2-chlorobenzoyl)-N'-[4-(3,5-dibromopyridyl-2-oxy)phenyl]urea
Substituted Benzoyl Urea Compound III (SBUC III):
 1-(4-trifluoromethoxyphenyl)-3-(2-chlorobenzoyl)urea
Phosphorous-Containing Compound I (PCC I):
 Triphenyl phosphate
Phosphorous-Containing Compound II (PCC II):
 S,S,S,-tributylphosphorotrithioate

EXAMPLES 1 THROUGH 39

PART A: PREPARATION OF SYNERGISTIC INSECTICIDAL COMPOSITIONS:

A series of compositions of this invention were prepared containing a 1-(mono-substituted phenyl)-3-benzoyl urea compounds and a phosphorous-containing compounds. Solutions of the urea compounds were first prepared by dissolving 0.1 gram of each compound into separate flasks (one compound per flask) containing 10 milliliters of acetone and 0.05 millileters of a commercially available alkylphenoxy polyethoxyethanol surfactant as an emulsifying or dispersing agent. The resulting solutions were then mixed with 90 milliliters of water to give 100 milliliters in each flask of an aqueous stock suspension containing separately 0.1 percent by weight of each urea compound and 0.1 percent by weight of each phosphorous-containing compound in finely divided form. The aqueous stock suspensions were diluted to appropriate concentrations in parts per million by weight (ppm) with water and then homogeneously blended at room temperature to give the chewing insect toxicant compositions in the weight proportion ratios shown in Table I below.

PART B: ACTIVITY OF THE CHEWING INSECT TOXICANT COMPOSITIONS

Selected compositions of this invention were evaluated with respect to their activity against a representative chewing insect, i.e., Southern armyworm. The test procedure was as follows:

Sourthern Armyworm Leaf Spray Bait Test

Larvae of the southern armyworm (*Spodoptera eridania*, (Cram.)), reared on Tendergreen bean plants at a temprature of 80±5° F. and a relative humidity of 50±5 percent, constituted the test insects. Potted Tendergreen bean plants of standard height and age were placed on a revolving turntable and sprayed with 100–110 milliliters of a composition prepared in Part A, a diluted aqueous suspension of a 1-(mono-substituted phenyl)-3-benzoyl urea compound prepared in Part A or a diluted aqueous suspension of a phosphorous-containing compound prepared in Part A by use of a Devilbiss spray gun set at 40 psig air pressure. This application, which lasted 25 seconds was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels. The results of this test are set forth in Table I below. A dash indicates that no test was performed. It should be understood that the Southern armyworm evaluated is representative of a wider variety of chewing insect which can be controlled by the compositions of this invention.

TABLE I

| COMPOSITIONS OF THIS INVENTION AND ACTIVITY THEREOF | | | | | | | | | | |
|---|---|---|---|---|---|---|---|---|---|---|
| EXAMPLE | 1 | 2 | 3 | 4 | 5 | 6 | 7 | 8 | 9 | 10 |
| Composition Identification: | | | | | | | | | | |
| 1-(Mono-Substituted Phenyl)-3-Benzoyl Urea Compound (SBUC) | I | I | I | I | I | I | I | II | II | II |
| Phosphorous-Containing Compound (PCC) | I | I | I | I | I | I | I | I | I | I |
| Composition Concentration: | | | | | | | | | | |
| 1-(Mono-Substituted Phenyl)-3-Benzoyl Urea Compound (ppm) | 60 | 30 | 15 | 7.5 | 3.8 | 1.9 | 0.95 | 20 | 10 | 5 |
| Phosphorous-Containing Compound (ppm) | 250 | 250 | 250 | 250 | 250 | 250 | 250 | 250 | 250 | 250 |
| Weight Proportion Ratio (SBUC/PCC) | 1/4.2 | 1/8.3 | 1/16.7 | 1/33.3 | 1/65.8 | 1/132 | 1/263 | 1/12.5 | 1/25 | 1/50 |
| Percent Mortality of Southern Armyworm: | | | | | | | | | | |
| 1-(Mono-Substituted Phenyl)-3-Benzoyl Urea Compound Alone | 80 | 50 | 18 | 15 | 0 | — | — | 90 | 76 | 67 |
| Phosphorous-Containing Compound Alone | 0 | 0 | 0 | 0 | 0 | 0 | 0 | 0 | 0 | 0 |
| Chewing Insect Toxicant Composition (SBUC + PCC) | — | — | — | 100 | 84 | 70 | 50 | — | 100 | 85 |
| EXAMPLE | 11 | 12 | 13 | 14 | 15 | 16 | 17 | 18 | 19 | 20 |
| Composition Identification: | | | | | | | | | | |
| 1-(Mono-Substituted Phenyl)-3-Benzoyl Urea Compound (SBUC) | II | II | II | III | III | III | III | III | III | I |
| Phosphorous-Containing Compound (PCC) | I | I | I | I | I | I | I | I | I | II |
| Composition Concentration: | | | | | | | | | | |
| 1-(Mono-Substituted Phenyl)-3-Benzoyl Urea Compound (ppm) | 2.5 | 1.25 | 0.63 | 80 | 40 | 20 | 10 | 5 | 2.5 | 15 |

TABLE I-continued
COMPOSITIONS OF THIS INVENTION AND ACTIVITY THEREOF

| | | | | | | | | | | |
|---|---|---|---|---|---|---|---|---|---|---|
| Phosphorous-Containing Compound (ppm) | 250 | 250 | 250 | 250 | 250 | 250 | 250 | 250 | 250 | 250 |
| Weight Proportion Ratio (SBUC/PCC) | 1/100 | 1/200 | 1/397 | 1/3.1 | 1/6.2 | 1/12.5 | 1/25 | 1/50 | 1/100 | 1/16.7 |
| Percent Mortality of Southern Armyworm: | | | | | | | | | | |
| 1-(Mono-Substituted Phenyl)-3-Benzoyl Urea Compound Alone | 30 | 10 | — | 89 | 80 | 51 | 38 | — | — | 18 |
| Phosphorous-Containing Compound Alone | 0 | 0 | 0 | 0 | 0 | 0 | 0 | 0 | 0 | 5 |
| Chewing Insect Toxicant Composition (SBUC + PCC) | 69 | 59 | 40 | 100 | 100 | 95 | 74 | 75 | 20 | — |

| EXAMPLE | 21 | 22 | 23 | 24 | 25 | 26 | 27 | 28 | 29 | 30 |
|---|---|---|---|---|---|---|---|---|---|---|
| Composition Identification: | | | | | | | | | | |
| 1-(Mono-Substituted Phenyl)-3-Benzoyl Urea Compound (SBUC) | I | I | I | I | I | I | II | II | II | II |
| Phosphorous-Containing Compound (PCC) | II | II | II | II | II | II | II | II | II | II |
| Composition Concentration: | | | | | | | | | | |
| 1-(Mono-Substituted Phenyl)-3-Benzoyl Urea Compound (ppm) | 7.5 | 3.8 | 0.62 | 0.31 | 0.15 | 0.075 | 5.0 | 2.5 | 1.25 | 0.62 |
| Phosphorous-Containing Compound (ppm) | 250 | 250 | 250 | 250 | 250 | 250 | 250 | 250 | 250 | 250 |
| Weight Proportion Ratio (SBUC/PCC) | 1/33.3 | 1/65.8 | 1/403 | 1/806 | 1/1667 | 1/3333 | 1/50 | 1/100 | 1/200 | 1/403 |
| Percent Mortality of Southern Armyworm: | | | | | | | | | | |
| 1-(Mono-Substituted Phenyl)-3-Benzoyl Urea Compound Alone | 15 | 0 | — | — | — | — | 67 | 30 | 10 | — |
| Phosphorous-Containing Compound Alone | 5 | 5 | 5 | 5 | 5 | 5 | 5 | 5 | 5 | 5 |
| Chewing Insect Toxicant Composition (SBUC + PCC) | — | — | 100 | 60 | 44 | 0 | — | — | 70 | 30 |

| EXAMPLE | 31 | 32 | 33 | 34 | 35 | 36 | 37 | 38 | 39 |
|---|---|---|---|---|---|---|---|---|---|
| Composition Identification: | | | | | | | | | | 
| 1-(Mono-Substituted Phenyl)-3-Benzoyl Urea Compound (SBUC) | II | II | III | III | III | III | III | III | III |
| Phosphorous-Containing Compound (PCC) | II | II | II | II | II | II | II | II | II |
| Composition Concentration: | | | | | | | | | |
| 1-(Mono-Substituted Phenyl)-3-Benzoyl Urea Compound (ppm) | 0.31 | 0.15 | 80 | 40 | 20 | 10 | 5 | 1.25 | 0.63 |
| Phosphorous-Containing Compound (ppm) | 250 | 250 | 250 | 250 | 250 | 250 | 250 | 250 | 250 |
| Weight Proportion Ratio (SBUC/PCC) | 1/806 | 1/1667 | 1/3.1 | 1/6.2 | 1/12.5 | 1/25 | 1/50 | 1/200 | 1/397 |
| Percent Mortality of Southern Armyworm: | | | | | | | | | |
| 1-(Mono-Substituted Phenyl)-3-Benzoyl Urea Compound Alone | — | — | 89 | 80 | 51 | 38 | — | — | — |
| Phosphorous-Containing Compound Alone | 5 | 5 | 5 | 5 | 5 | 5 | 5 | 5 | 5 |
| Chewing Insect Toxicant Composition (SBUC + PCC) | 10 | 0 | — | 97 | 93 | 90 | 68 | 79 | 47 |

The results of Table I clearly demonstrate that selected chewing insect toxicant compositions of this invention possess greatly enhanced biological activity against the Southern armyworm in comparison with the combined additive biological activity exhibited by the 1-(mono-substituted phenyl)-3-benzoyl urea compound alone and the phosphorous-containing compound alone as specified concentration amounts.

TABLE II
SOUTHERN ARMYWORM TOXICITY DATA

| | | % Mortality | | |
|---|---|---|---|---|
| Urea Compound | Concentration in ppm | Urea Compound alone | *Synergist alone (250 ppm) | Urea Compound + Synergist |
| (1) diflubenzuron | 60 | 80 | 0 | — |
| | 30 | 50 | | — |
| | 15 | 18 | | — |
| | 7.5 | 15 | | 100 |
| | 3.8 | 0 | | 84 |
| | 1.9 | — | | 70 |
| | 0.95 | — | | 50 |
| (2) N—(2-chlorobenzoyl) N'—[4-(3-,5-dibomo-pyridyl-2-oxy)phenyl] urea | 20 | 90 | | — |
| | 10 | 76 | | 100 |
| | 5 | 67 | | 85 |
| | 2.5 | 30 | | 69 |
| | 1.25 | 10 | | 59 |
| | 0.63 | — | | 40 |
| (3) 1-(4-trifluoro-methoxyphenyl)-3-(2-chlorobenzoyl) urea | 80 | 89 | | 100 |
| | 40 | 80 | | 100 |
| | 20 | 51 | | 95 |
| | 10 | 38 | | 74 |
| | 5 | — | | 75 |
| | 2.5 | — | | 20 |
| (4) N—(2,6 difluorobenzoyl) N'—[3,5-dichloro-4-(3-chloro-5-trifluoro-methylpyridyl-2-oxy) | 3 | 100 | | 100 |
| | 1.5 | 98 | | 95 |
| | 0.8 | 78 | | 77 |
| | 0.4 | 42 | | 71 |

TABLE II-continued

SOUTHERN ARMYWORM TOXICITY DATA

| Urea Compound | Concentration in ppm | % Mortality Urea Compound alone | *Synergist alone (250 ppm) | Urea Compound + Synergist |
|---|---|---|---|---|
| phenyl urea] | 0.2 | 51 | | 30 |
| (5) 1-[3,5 dichloro-4-(4-nitrophenyoxy) phenyl]-3-(2-chlorobenzoyl) urea | 3.0 | 100 | | — |
| | 1.5 | 59 | | 90 |
| | 0.8 | 40 | | 43 |
| | 0.4 | 27 | | 25 |
| | 0.2 | 10 | | 15 |

*Triphenyl phosphate

TABLE III

SOUTHERN ARMYWORM TOXICITY DATA

| Urea Compound | Concentration in ppm | % Mortality Urea Compound alone | *Synergist alone (250 ppm) | Urea Compound + Synergist |
|---|---|---|---|---|
| (1) diflubenzuron | 15 | 18 | 5 | — |
| | 7.5 | 15 | | — |
| | 3.8 | 0 | | — |
| | 0.62 | — | | 100 |
| | 0.31 | — | | 60 |
| | 0.15 | — | | 44 |
| | 0.075 | — | | 0 |
| (2) N—(2-chlorobenzoyl)N'—[4-(3,5-dibromopyridyl-2-oxy)phenyl]urea | 5.0 | 67 | — | — |
| | 2.5 | 30 | | — |
| | 1.25 | 10 | | 70 |
| | 0.62 | 30 | | 30 |
| | 0.31 | — | | 10 |
| | 0.15 | — | | 0 |
| (3) 1-(4-trifluoromethoxyphenyl)-3-(2-chlorobenzoyl)urea | 80 | 89 | | — |
| | 40 | 80 | | 97 |
| | 20 | 51 | | 93 |
| | 10 | 38 | | 90 |
| | 5 | — | | 68 |
| | 1.25 | — | | 79 |
| | 0.63 | — | | 47 |
| (4) N—(2,6 difluorobenzoyl)N'—[3,5-dichloro-4-(3-chloro-5-trifluoromethyl-pyridyl-2-oxy)phenyl urea] | 3 | 100 | | — |
| | 1.5 | 98 | | — |
| | 0.8 | 78 | | — |
| | 0.4 | 42 | | 55 |
| | 0.2 | 51 | | 21 |
| (5) 1-[3,5 dichloro-4-(4-nitrophenoxy) phenyl]-3-(2-chlorobenzoyl) urea | 3.0 | 100 | | 88 |
| | 1.5 | 59 | | 38 |
| | 0.8 | 40 | | 50 |
| | 0.4 | 27 | | 0 |
| | 0.2 | 10 | | 13 |

*S,S,S—tributylphosphorotrithioate

Tables II and III show quite clearly not only the significant enhancement of biological activity realizable with the combinations of the instant invention but also that this toxicological enhancement on chewing insects is limited to phenyl, benzoyl urea compounds that have mono-substituents on the aniline portion of the molecule.

I claim:

1. A chewing insect toxicant composition comprising a non-toxic carrier and an insecticidally effective amount of (1) a 1-(mono-substituted phenyl)-3-benzoyl urea compound having the formula:

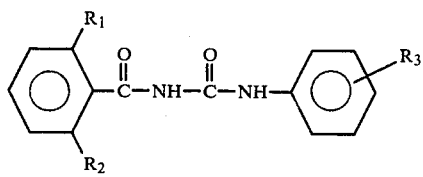

in admixture with (2) a phosphorous-containing compound having the formula:

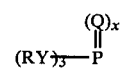

wherein:
R is:
  an alkyl group having no more than ten carbon atoms, or
  aryl or aryl substituted with alkyl or alkoxy;
R₁ and R₂ are independently:
  hydrogen, or halogen;
R₃ is:
  halogen,
  an alkyl, haloalky, alkoxy, or haloalkoxy group having no more than eight carbon atoms,
  a pyridyloxy group, or
  a halopyridyloxy group;
Y and Q are independently:

oxygen, or
sulfur; and
x is:
zero, or
one
wherein the weight proportion ratio of the 1-(monosubstituted phenyl)-3-benzoyl urea compound to the phosphorous containing compound is from about 1:5 to about 1:50,000 parts by weight respectively.

2. A composition as defined in claim 1 wherein R is methyl, ethyl, isopropyl, butyl, phenyl or tolyl.

3. A composition as defined in claim 2 wherein $R_1$ and $R_2$ are independently hydrogen, chloro or fluoro.

4. A composition as defined in claim 3 wherein $R_3$ is chloro, trifluoromethyl, trifluoromethoxy or 3,5-dibromopyridyl-2-oxy.

5. A composition as defined in claim 4 wherein Q is oxygen and Y is sulfur.

6. A composition as defined in claim 4 wherein Q and Y are oxygen.

7. A composition as defined in claims 6 or 7 wherein x is one.

8. A chewing insect toxicant composition as defined in claim 1 comprising (1) a 1-(mono-substituted phenyl)-3-benzoyl urea compound having the formula:

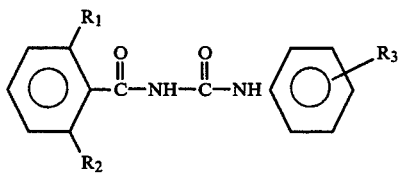

in admixture with (2) an amount sufficient to enhance the chewing insect toxicity of said urea compound of a phosphorous-containing compound having the formula:

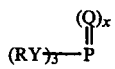

wherein:
R is:
methyl, ethyl, isopropyl, butyl, or phenyl or tolyl;
$R_1$ and $R_2$ are independently:
hydrogen, or
chloro or fluoro;
$R_3$ is:
chloro,
trifluoromethyl,
trifluoromethoxy, or
3,5-dibromopyridyl-2-oxy;
Y and Q are independently:
oxygen, or
sulfur; and
x is:
one.

9. A chewing insect toxicant composition as defined in claim 1 comprising (1) a 1-(mono-substituted phenyl)-3-benzoyl urea compound selected from the group consisting of N-(2,6-difluorobenzoyl)-N'-(4-chlorophenyl)urea, N-(2-chlorobenzoyl)-N'-[4-(3,5-dibromopyridyl-2-oxy) phenyl]urea and 1-(4-trifluoromethoxyphenyl)-3-(2-chlorobenzoyl) urea in admixture with (2) and amount sufficient to enhance the chewing insect toxicity of said urea compound of a phosphorous-containing compound selected from the group consisting of tri-phenyl phosphate and S,S,S-tributylphosphorotrithioate.

10. A chewing insect toxicant composition as defined in claim 1 comprising (1) N-(2,6-difluorobenzoyl)-N'-(4-chlorophenyl)urea in admixture with (2) an amount sufficient to enhance the chewing insect toxicity of said urea compound of triphenyl phosphate.

11. A chewing insect toxicant composition as defined in claim 1 comprising (1) N-(2-chlorobenzoyl)-N'-[4-(3,5-dibromopyridyl-2-oxy) phenyl]urea in admixture with (2) an amount sufficient to enhance the chewing insect toxicity of said urea compound of triphenyl phosphate.

12. A chewing insect toxicant composition as defined in claim 1 comprising (1) 1-(4-trifluoromethoxyphenyl)-3-(2-chlorobenzoyl)urea in admixture with (2) an amount sufficient to enhance the chewing insect toxicity of said urea compound of triphenyl phosphate.

13. A chewing insect toxicant composition ad defined in claim 1 comprising (1) N-(2,6-difluorobenzoyl)-N'-(4-chlorophenyl)urea in admixture with (2) an amount sufficient to enhance the chewing insect toxicity of said urea compound of S,S,S-tributylphosphorotrithioate.

14. A chewing insect toxicant composition as defined in claim 1 comprising (1) N-(2-chlorobenzoyl)-N'-[4-(3,5-dibromopyridyl-2-oxy) phenyl]urea in admixture with (2) an amount sufficient to enhance the chewing insect toxicity of said urea compound of S,S,S-tributylphosphorotrithioate.

15. A chewing insect toxicant composition as defined in claim 1 comprising (1) 1-(4-trifluoromethoxyphenyl-3-(2-chlorobenzoyl)urea in admixture with (2) an amount sufficient to enhance the chewing insect toxicity of said urea compound of S,S,S-tributylphosphorotrithioate.

16. A chewing insect toxicant composition comprising an acceptable carrier and as the active toxicant an effective amount of the composition as defined in claim 1.

17. A composition as defined in claim 16 wherein R is methyl, ethyl, isopropyl, butyl, phenyl or tolyl.

18. A composition as defined in claim 17 wherein $R_1$ and $R_2$ are independently hydrogen, chloro or fluoro.

19. A composition as defined in claim 18 wherein $R_3$ is chloro, trifluoromethyl, trifluoromethoxy, or 3,5-dibromopyridyl-2-oxy.

20. A composition as defined in claim 19 wherein Q is oxygen and Y is sulfur.

21. A composition as defined in claim 19 wherein Q and Y are oxygen.

22. A composition as defined in claims 20 or 21 wherein x is one.

23. A method of controlling chewing insects which comprises subjecting them to an effective amount of the composition as defined in claim 1.

24. A method as defined in claim 23 wherein R is methyl, ethyl, isopropyl, butyl, phenyl, or tolyl.

25. A method as defined in claim 24 wherein $R_1$ and $R_2$ are independently hydrogen, chloro or fluoro.

26. A method as defined in claim 25 wherein $R_3$ is chloro, trifluoromethyl, trifluoromethoxy, or 3,5-dibromopyridyl-2-oxy.

27. A method as defined in claim 26 wherein Q is oxygen and Y is sulfur.

28. A method as defined in claim 27 wherein Q and Y are oxygen.

29. A method as defined in claims 27 or 28 wherein x is one.

30. A method of controlling chewing insects which comprising subjecting them to an effective amount of the composition as defined in claim 8.

31. A method of controlling chewing insects which comprises subjecting them to an effective amount of the composition as defined in claim 9.

32. A method of controlling chewing insects which comprises subjecting them to an effective amount of the composition as defined in claim 10.

33. A method of controlling chewing insects which comprises subjecting them to an effective amount of the composition as defined in claim 11.

34. A method of controlling chewing insects which comprises subjecting them to an effective amount of the composition as defined in claim 12.

35. A method of controlling chewing insects which comprises subjecting them to an effective amount of the composition as defined in claim 13.

36. A method of controlling chewing insects which comprises subjecting them to an effective amount of the composition as defined in claim 14.

37. A method of controlling chewing insects which comprises subjecting them to an effective amount of the composition as defined in claim 15.

* * * * *